United States Patent
Sekiguchi et al.

(10) Patent No.: US 9,326,662 B2
(45) Date of Patent: May 3, 2016

(54) PROBE AND ENDOSCOPE

(71) Applicant: OLYMPUS CORPORATION, Tokyo (JP)

(72) Inventors: Masahiko Sekiguchi, Akiruno (JP); Fumiyuki Onoda, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/070,915

(22) Filed: Nov. 4, 2013

(65) Prior Publication Data
US 2014/0100463 A1   Apr. 10, 2014

Related U.S. Application Data
(63) Continuation of application No. PCT/JP2013/061381, filed on Apr. 17, 2013.

(30) Foreign Application Priority Data
Jul. 13, 2012  (JP) ................. 2012-157455

(51) Int. Cl.
A61B 1/00 (2006.01)
A61B 8/12 (2006.01)
A61B 5/06 (2006.01)
A61B 8/00 (2006.01)
A61B 1/018 (2006.01)
A61B 1/04 (2006.01)

(52) U.S. Cl.
CPC ......... *A61B 1/00055* (2013.01); *A61B 1/00158* (2013.01); *A61B 1/018* (2013.01); *A61B 5/062* (2013.01); *A61B 8/12* (2013.01); *A61B 8/4444* (2013.01); *A61B 8/4483* (2013.01); *A61B 8/4494* (2013.01); *A61B 8/445* (2013.01)

(58) Field of Classification Search
CPC ............... A61B 1/00055; A61B 1/018; A61B 1/00158; A61B 8/4483
USPC ......... 600/114, 117, 118, 145, 424, 103, 104, 600/462; 604/526, 528
See application file for complete search history.

(56) References Cited

U.S. PATENT DOCUMENTS 5,997,473 A * 12/1999 Taniguchi et al. ............ 600/117
2002/0128537 A1   9/2002 Watanabe et al.
(Continued)

FOREIGN PATENT DOCUMENTS

JP   07-111969 A   5/1995
JP   10-075929 A   3/1998
(Continued)

Primary Examiner — Anhtuan T Nguyen
Assistant Examiner — Timothy J Neal
(74) Attorney, Agent, or Firm — Scully, Scott, Murphy & Presser, PC

(57) ABSTRACT

A probe is a probe insertable through a channel provided in an endoscope insertion portion. The probe is provided with a plurality of accommodation portions for accommodating a plurality of coil units having a predetermined length and a predetermined height, and a plurality of axial portions. Each accommodation portion includes a base portion having a length substantially equal to the predetermined length in a longitudinal direction of the probe, and two wall portions provided to stand upright at both ends of the base portion in the longitudinal direction at a height substantially equal to the predetermined height from the base portion, and the base portion and the wall portions are integrally formed. The plurality of axial portions extend from the wall portions in the longitudinal direction and connect between the plurality of accommodation portions.

16 Claims, 14 Drawing Sheets

(56) References Cited

U.S. PATENT DOCUMENTS

2003/0028096 A1 2/2003 Niwa et al.
2003/0195388 A1* 10/2003 Niwa et al. .................. 600/117
2005/0070790 A1* 3/2005 Niwa et al. .................. 600/117

FOREIGN PATENT DOCUMENTS

| | | |
|---|---|---|
| JP | 2002-263056 A | 9/2002 |
| JP | 2003-047586 A | 2/2003 |
| JP | 2011-254874 A | 12/2011 |

* cited by examiner

PROBE AND ENDOSCOPE

CROSS REFERENCE TO RELATED APPLICATION

This application is a continuation application of PCT/JP2013/061381 filed on Apr. 17, 2013 and claims benefit of Japanese Application No. 2012-157455 filed in Japan on Jul. 13, 2012, the entire contents of which are incorporated herein by this reference.

BACKGROUND OF THE INVENTION

1. Field of the Invention

The present invention relates to a probe and an endoscope, and more particularly, to a probe and an endoscope equipped with a plurality of electronic parts.

2. Description of the Related Art

Conventionally, endoscope insertion shape observation apparatuses are known which are designed to display an insertion shape of an endoscope inserted into a subject on a monitor.

For example, Japanese Patent Application Laid-Open Publication No. 07-111969 discloses an endoscope insertion state detection apparatus that provides a plurality of coils in an endoscope insertion portion and detects magnetic fields generated in the plurality of coils using magnetic field detection means provided outside the endoscope. The endoscope insertion state detection apparatus calculates a position of each coil in a three-dimensional space from the detected magnetic fields, determines a shape of the endoscope insertion portion based on the positions of the plurality of magnetic coils and through position estimation among the coils, and displays the shape on a monitor.

Furthermore, an endoscope insertion shape observation probe having an elongated shape is also known which is, without incorporating a plurality of coils in an endoscope insertion portion, independent of the insertion portion, inserted from a forceps insertion port of the endoscope and insertable through a treatment instrument insertion channel in the endoscope insertion portion.

The endoscope insertion shape observation probe is made up of rigid coils, each of which is a thin copper wire wound around an iron core and flexible tubes, the coils and the tubes being alternately arranged and connected together to form a single elongated probe. Each coil and a neighboring tube are connected together by bonding an end face of a rigid portion of the coil end and an end face of the tube using an adhesive.

SUMMARY OF THE INVENTION

A probe according to an aspect of the present invention is a probe insertable through a channel provided in an endoscope insertion portion or incorporated in the endoscope insertion portion, including a plurality of accommodation portions to accommodate an electronic part having a predetermined length and a predetermined height, provided with a base portion, the base portion having a length substantially equal to the predetermined length in a longitudinal direction of the probe, and two wall portions provided to stand upright at both ends of the base portion in the longitudinal direction at a height substantially equal to the predetermined height from the base portion, the base portion and the wall portions being integrally formed, and a plurality of axial portions that extend from the wall portions in the longitudinal direction and connect between the plurality of accommodation portions.

An endoscope according to an aspect of the present invention incorporates the probe of the present invention in the endoscope insertion portion.

DETAILED DESCRIPTION OF THE PREFERRED EMBODIMENTS

Hereinafter, embodiments of the present invention will be described with reference to the accompanying drawings.

Hereinafter, a probe according to embodiments of the present invention will be described. In the following description, since drawings based on the respective embodiments are schematic ones, these drawings may include relations between a thickness and a width of each component, ratio in thickness between the respective components or the like which are different from the actual ones, and also include components whose dimensional relations and ratios are different among those drawings.

First Embodiment

Figure 1:
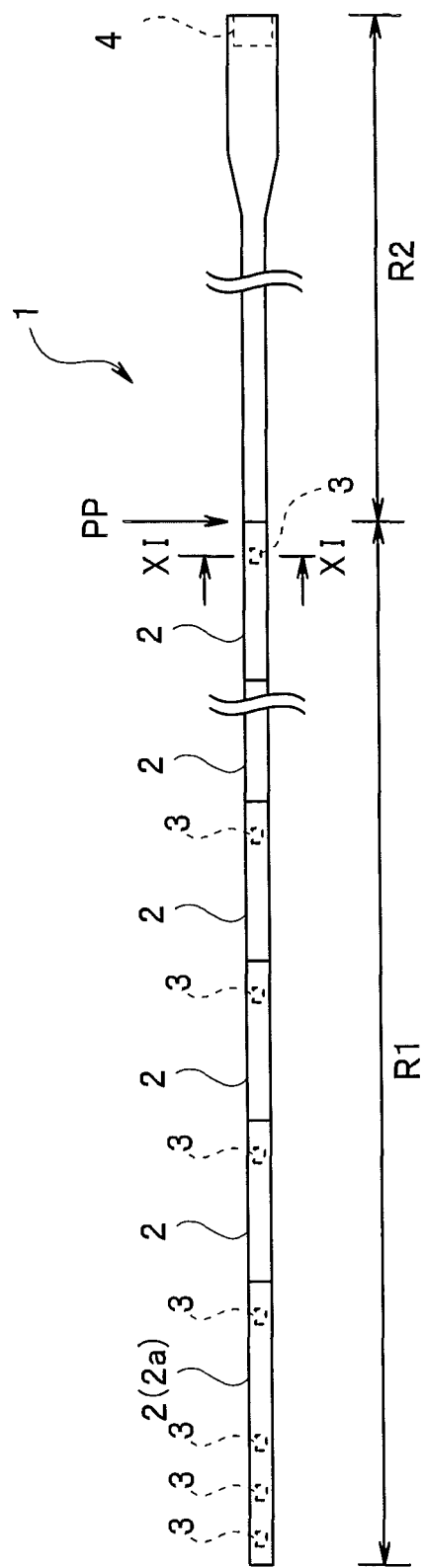
FIG. 1 is a schematic configuration diagram illustrating an overall configuration of a probe according to a first embodiment of the present invention.

FIG. 1 is a schematic configuration diagram illustrating an overall configuration of a probe according to the present embodiment.

The probe 1 is an endoscope insertion shape observation probe as a medical probe. The probe 1 is a probe insertable through a channel provided in an endoscope insertion portion or incorporated in the endoscope insertion portion. The probe 1 has a portion on a distal end side connecting a plurality of electronic part accommodation members (hereinafter, simply referred to as "accommodation members") 2, each of which can accommodate an electronic part, the probe 1 being an elongated and flexible instrument whose outer circumferential portion is covered with a sheath member. Note that in FIG. 1, the sheath member is not shown.

A distal end side portion R1 of the probe 1 is constructed of a plurality of flexible and elongated accommodation members 2 connected together to accommodate a plurality of electronic parts as will be described later. A proximal end side portion R2 of the probe 1 is also bendable but since it contains a wire member as will be described later, it is more rigid than the distal end side portion R1.

Among the plurality of accommodation members 2 of the distal end side portion R1, an accommodation member closest to the distal end of the probe 1 (hereinafter, referred to as "distal end accommodation member") 2a is longer than other accommodation members 2 in an axial direction. Each accommodation member 2 including the distal end accommodation member 2a is provided with one or two or more coil units 3 which are electronic parts. Two wires extend from each coil unit 3 and all wires of the all coil units 3 are connected to a connector 4 at the proximal end portion of the probe 1.

The connector 4 of the probe 1 is connected to an endoscope insertion shape observation apparatus (not shown). The endoscope insertion shape observation apparatus (not shown) calculates the position of each coil unit 3 in a three-dimensional space from a detected magnetic field, determines the shape of the endoscope insertion portion from the positions of the plurality of magnetic coils and through position estimation among the coils and displays the shape on a monitor.

Figure 2:
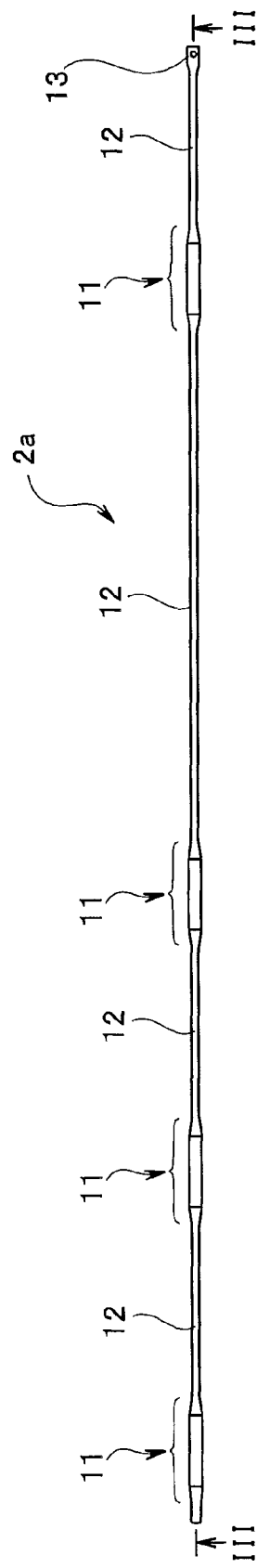
FIG. 2 is a plan view of a distal end accommodation member 2a of the probe 1 according to the first embodiment of the present invention.
Figure 3:
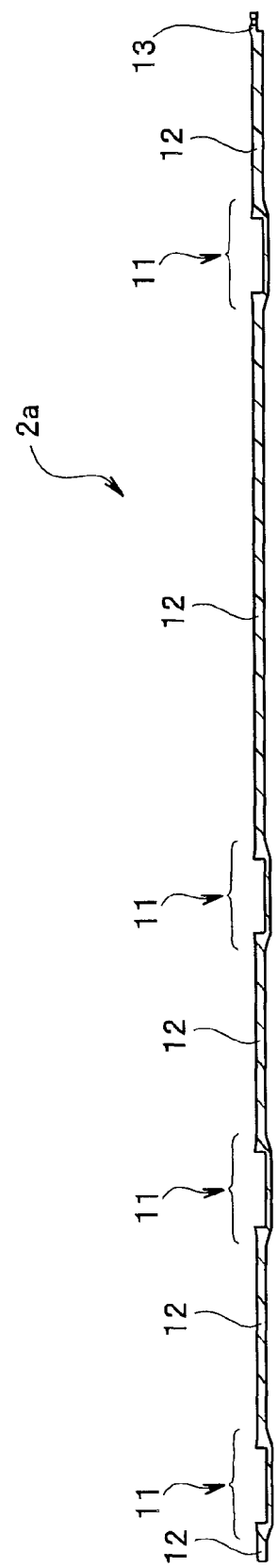
FIG. 3 is a cross-sectional view of the distal end accommodation member 2a along a line III-III in FIG. 2.

FIG. 2 is a plan view of the distal end accommodation member 2a of the probe 1. FIG. 3 is a cross-sectional view of the distal end accommodation member 2a along a line III-III in FIG. 2.

The distal end accommodation member 2a which is an electronic part accommodation member is made of elongated solid silicon rubber and can accommodate, that is, mount four coil units 3. The distal end accommodation member 2a is formed through integral molding using a molding technique such as injection molding. The distal end accommodation member 2a has a plurality of coil accommodation portions (hereinafter, referred to as "accommodation portions") 11 to accommodate the plurality of coil units 3. As shown in FIG. 2 and FIG. 3, the distal end accommodation member 2a has four accommodation portions 11 and each accommodation portion 11 has a concave portion formed in part of the distal end accommodation member 2a.

The probe 1 includes the axial portions 12 at the distal end portion of the distal end accommodation member 2a, between neighboring accommodation portions 11 and at the proximal end portion. The axial portion 12 has a columnar shape. The axial portion 12 on the distal end side of the distal end accommodation member 2a has a shape of the distal end with rounded corners. The axial portion 12 of the distal end accommodation member 2a on the proximal end side is provided with a connection portion 13. That is, the distal end accommodation member 2a has a plurality of accommodation portions 11 between the axial portion 12 on the distal end side and the axial portion 12 on the proximal end side, and the connection portion 13 for connection with another accommodation member 2 on the proximal end side.

When the probe 1 is used while being inserted through a treatment instrument insertion channel of the endoscope, the distal end portion of the probe 1 is located at a bending portion of the endoscope insertion portion on the distal end side. For this reason, the distance between the coil units 3 on the distal end side of the distal end accommodation member 2a is smaller than the distance between the coil units 3 of the distal end accommodation member 2a on the proximal end side to allow the bending shape on the distal end side of the bending portion of the endoscope insertion portion to be accurately determined. As shown in FIG. 2 and FIG. 3, the distance between the accommodation portions 11 accommodating three coil units 3 on the distal end side in the distal end accommodation member 2a is smaller than the distance between the two accommodation portions 11 on the proximal end side.

Figure 4:
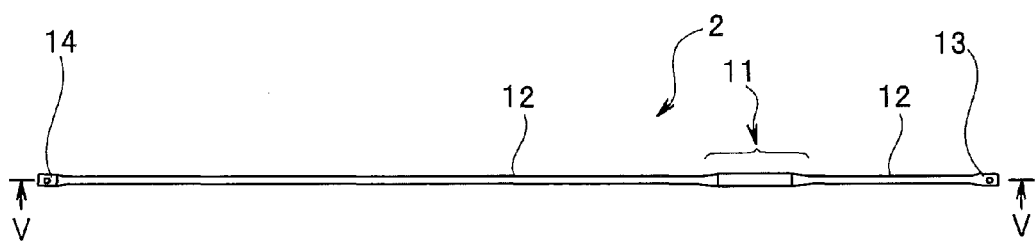
FIG. 4 is a plan view of an accommodation member 2 other than the distal end accommodation member 2a according to the first embodiment of the present invention.
Figure 5:
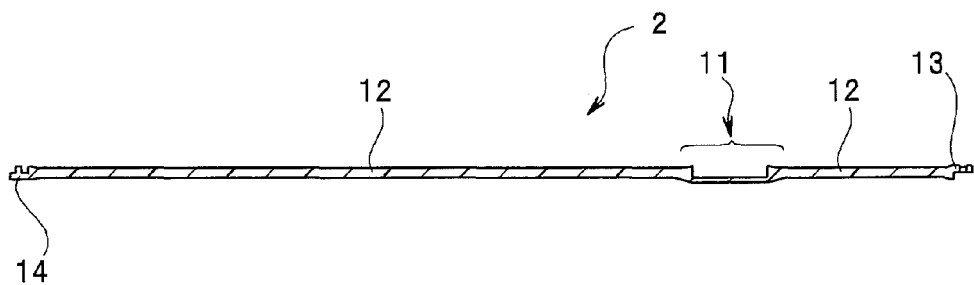
FIG. 5 is a cross-sectional view of the accommodation member 2 along a line V-V in FIG. 4.
Figure 6:
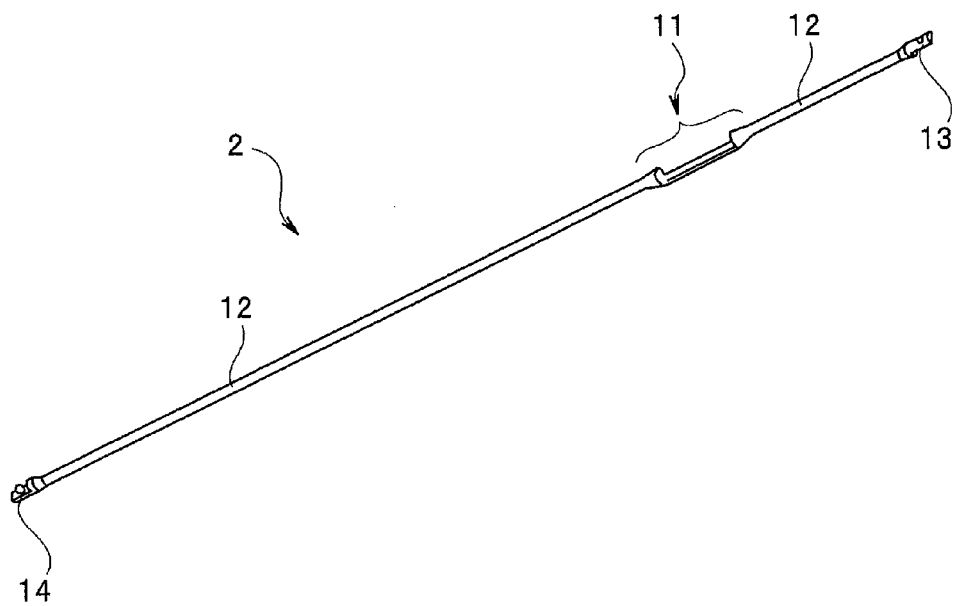
FIG. 6 is a perspective view of the accommodation member 2 in FIG. 4.

FIG. 4 is a plan view of the accommodation member 2 other than the distal end accommodation member 2a. FIG. 5 is a cross-sectional view of the accommodation member 2 along a line V-V in FIG. 4. FIG. 6 is a perspective view of the accommodation member 2 in FIG. 4.

The accommodation member 2 which is an electronic part accommodation member is made of elongated and solid silicon rubber as in the case of the distal end accommodation member 2a. The accommodation member 2 is also formed through integral molding using a molding technique such as injection molding. As described above, the accommodation member 2 has a connection portion 14 at the distal end of the accommodation member 2 for connection with another accommodation member 2 and is provided with the connection portion 13 on the proximal end side of the accommodation member 2. The connection portion 13 of the accommodation member 2 has the same shape as that of the connection portion 13 of the distal end accommodation member 2a, and the axial portion 12 of the accommodation member 2 has the same shape as that of the axial portion 12 of the distal end accommodation member 2a.

The accommodation member 2 is provided with an accommodation portion 11 to accommodate one coil unit 3. The accommodation portion 11 of the accommodation member 2 has the same shape as that of each accommodation portion 11 of the distal end accommodation member 2a. That is, the difference between the distal end accommodation member 2a and the accommodation member 2 other than the distal end accommodation member 2a lies in the number of the accommodation portions 11, the number and lengths of the axial portions 12 and the presence or absence of the connection portion 14. In the probe 1, the distances between the plurality of coil units 3 provided closer to the proximal end side than the coil unit 3 at the proximal end of the distal end accommodation member 2a are equal.

Note that the accommodation member 2 including the distal end accommodation member 2a is made of silicon rubber here, but other materials may also be used.

As described above, the probe 1 is configured by connecting a plurality of accommodation members 2 (including the distal end accommodation member 2a) formed by uniting one or two or more accommodation portions 11 and two or more axial portions 12. Each accommodation member 2 (including the distal end accommodation member 2a) has connection portions 13 and 14 that connect between the accommodation members.

Next, a configuration of the accommodation portion 11 provided for the distal end accommodation member 2a and the accommodation member 2 will be described.

Figure 7:
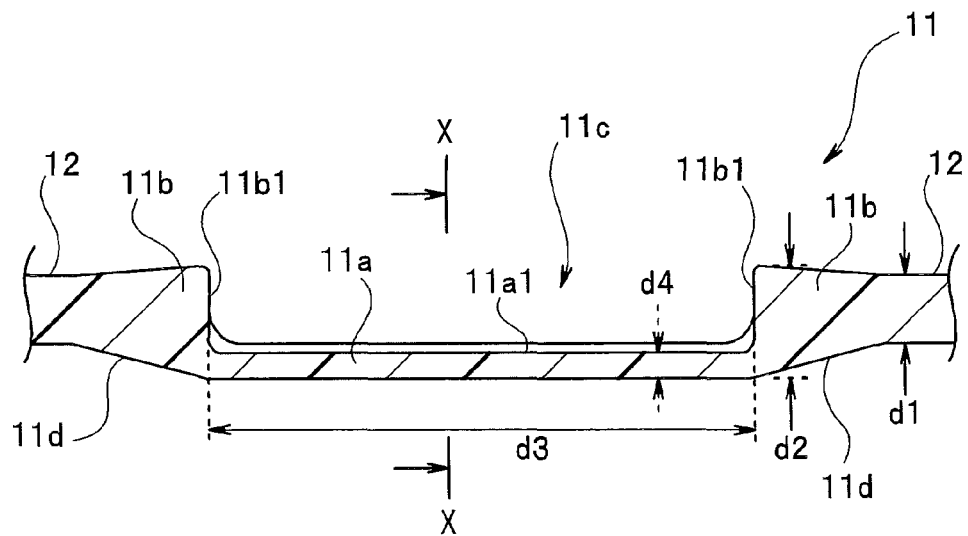
FIG. 7 is a cross-sectional view of an accommodation portion 11 along a longitudinal axis direction according to the first embodiment of the present invention.

FIG. 7 is a cross-sectional view of the accommodation portion 11 along a longitudinal direction.

As shown in FIG. 7, the accommodation portion 11 which is an electronic part accommodation portion has a base portion 11a and two wall portions 11b provided to stand upright upward from the base portion 11a at both ends in the longitudinal direction of the base portion 11a. More specifically, to accommodate the coil unit 3 which is an electronic part having a predetermined length and a predetermined height, the accommodation portion 11 has the base portion 11a having a length substantially equal to the predetermined length in the longitudinal direction of the probe 1 and the two wall portions 11b provided to stand upright at a height substantially equal to the predetermined height of the coil unit 3 from the base portion 11a at both ends of the base portion 11a in the longitudinal direction of the probe 1. Furthermore, the accommodation portion 11 has the integrally formed base portion 11a and wall portion 11b.

A bottom surface 11a1 of the base portion 11a and two opposite wall surfaces 11b1 of the two wall portions 11b form a concave portion 11c which constitutes an accommodation space to accommodate the coil unit 3. A tapered portion 11d which is an expansion portion is provided between the wall portion 11b and the axial portion 12. That is, the wall portion 11b has the tapered portion 11d in the longitudinal direction of the probe 1. The tapered portion 11d has such a shape that an outside size gradually decreases from the wall surface 11b1 toward the axial portion 12. As shown in FIG. 7, the tapered portion 11d is provided for both wall portions 11b and the cross-sectional shape on the wall surface 11b1 side is greater than the cross-sectional shape on the axial portion 12 side.

The axial portion 12 extends in the longitudinal direction of the probe 1 from the wall portion 11b and connects between a plurality of accommodation portions 11.

The bottom surface 11a1 of the base portion 11a has a trough-like curved surface shape along the axial direction of the probe 1. Sizes of the distal end accommodation member 2a and the accommodation member 2 are, for example, as follows. A diameter d1 of the axial portion 12 is, for example, 0.5 mm to 2 mm A maximum diameter d2 of the tapered portion 11d is, for example, 1 mm to 2 mm A length d3 of the concave portion 11c of the accommodation portion 11 in the axial direction is, for example, 5 mm to 15 mm. A thickness d4 of a thin portion of the base portion 11a of the concave portion 11c of the accommodation portion 11 is, for example, 0.2 mm to 0.5 mm.

Figure 8:
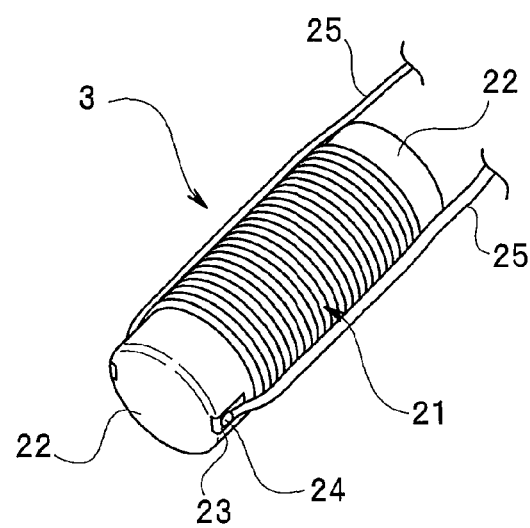
FIG. 8 is a perspective view of a coil unit 3 according to the first embodiment of the present invention.

FIG. 8 is a perspective view of the coil unit 3. As shown in FIG. 8, the coil unit 3 as an electronic part has a columnar shape as a whole and includes a magnetic coil 21 which is a thin copper wire wound around an iron core (not shown) (hereinafter, simply referred to as "coil"), insulating portions 22 provided at both ends of the coil 21, two land portions 23 provided on an outer circumferential surface of the insulating portion 22 on the distal end side to which both ends of the coil 21 are connected, and two wires 25 connected by solder 24 to the two land portions 23. The two land portions 23 are formed on opposite sides of a circumferential surface of the columnar insulating portions 22. When the coil unit 3 is accommodated in the accommodation member 2, the two wires 25 extend from the coil unit 3 toward the proximal end direction of the probe 1.

There is a conventional coil unit from which a terminal connected to both ends of a coil protrudes. In such a case, when wires are soldered to the terminal, it is necessary to perform operation such as application of an adhesive for reinforcing the terminal. However, as described above, since the land portions 23 are formed in the insulating portion 22 which is a cylindrical portion wound with the coil, no such reinforcement procedure for soldering is necessary. Moreover, since the land portions 23 are formed in the insulating portion 22, it is possible to reduce the length of the coil unit 3 in the longitudinal direction.

Figure 9:
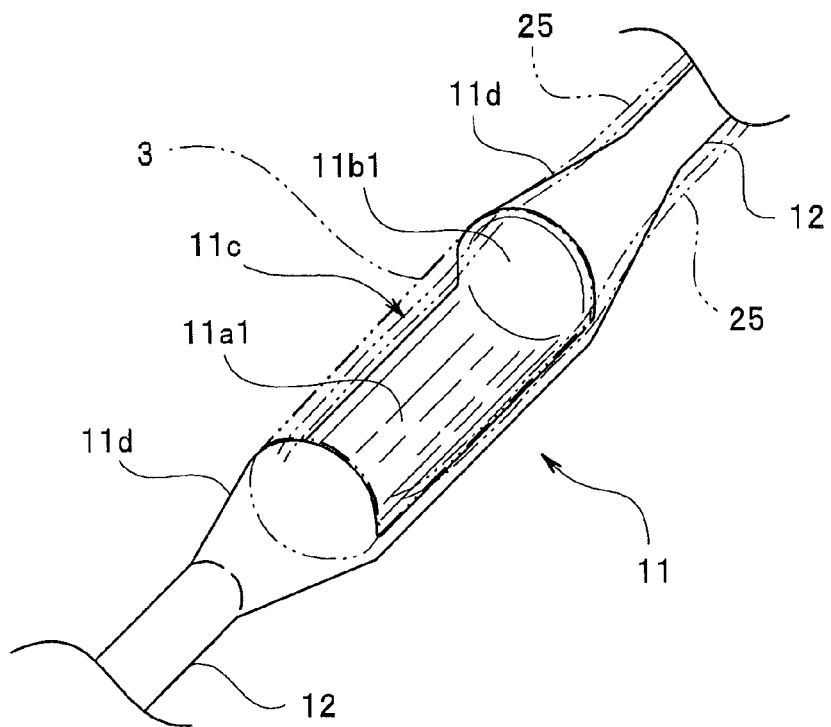
FIG. 9 is a perspective view of the accommodation portion 11 according to the first embodiment of the present invention.
Figure 10:
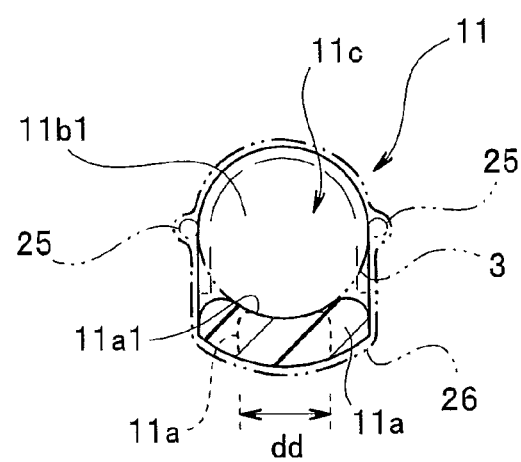
FIG. 10 is a cross-sectional view of the accommodation portion 11 along a line X-X in FIG. 7.

FIG. 9 is a perspective view of the accommodation portion 11. FIG. 10 is a cross-sectional view of the accommodation portion 11 along a line X-X in FIG. 7. The coil unit 3 is accommodated so as to fit into the concave portion 11c of the accommodation portion 11.

Furthermore, as shown in FIG. 10, the shape of the bottom surface 11a1 of the base portion 11a in a cross section orthogonal to the axial direction of the distal end accommodation member 2a matches the shape of an outer circumferential surface of the coil 21 of the columnar coil unit 3. Therefore, when the coil unit 3 which is an electronic part is placed and accommodated in the concave portion 11c, the outer circumferential surface of the coil 21 comes into close contact with the bottom surface 11a1. That is, the contact surface of the base portion 11a that contacts the coil unit 3 when the coil unit 3 which is an electronic part is placed has a curved surface along the outer circumferential surface of the coil unit 3.

Furthermore, when the coil unit 3 is accommodated in the concave portion 11c and the wall surface 11b1 of the wall portion 11b is viewed from the axial direction of the distal end accommodation member 2a, an outside shape of the upper side of the wall surface 11b1 (that is, an edge shape) matches the shape of the outer circumferential surface of the coil 21 of the coil unit 3. That is, the wall portion 11b partially has an edge shape along the cross-sectional shape of the coil unit 3 orthogonal to the longitudinal direction of the probe 1 when the coil unit 3 which is an electronic part is placed.

Thus, as shown in FIG. 10, when the cross-sectional shape of the coil unit 3 orthogonal to the longitudinal direction of the probe 1 is circular when the coil unit 3 is placed, the cross-sectional shape of the curved surface of the bottom surface 11a1 orthogonal to the longitudinal direction matches an arc which is a part of the circle and the edge shape of the wall portion 11b also matches an arc of another part of the circle.

Note that as shown by a two-dot dashed line in FIG. 10, a thermal contraction tube 26 may also be provided so as to cover the perimeter of the accommodation portion 11 to increase rigidity of the accommodation portion 11.

Furthermore, as shown by a dotted line in FIG. 10, a width dd in a direction orthogonal to the axial direction of the base portion 11a may be shorter than the diameter of the coil unit 3.

Figure 11:
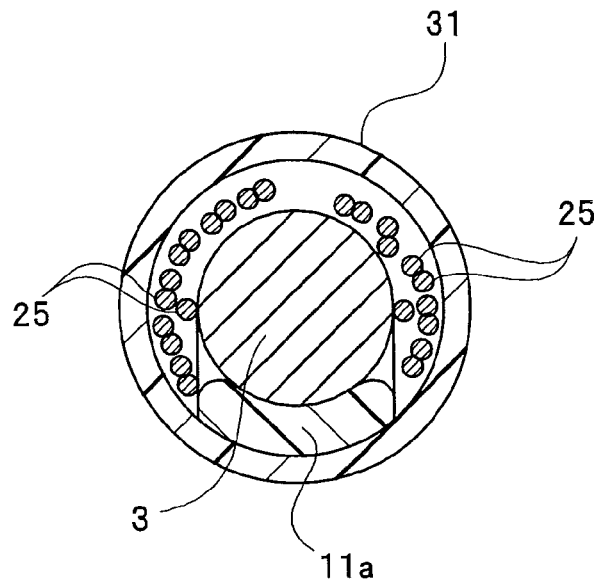
FIG. 11 is a cross-sectional view of the probe 1 along a line XI-XI in FIG. 1.

FIG. 11 is a cross-sectional view of the probe 1 along a line XI-XI in FIG. 1. As shown in FIG. 11, the coil unit 3 is accommodated in the accommodation portion 11 so that part thereof comes into close contact with the bottom surface 11a1 of the base portion 11a of the accommodation portion 11.

The outer circumferential portion of the accommodation portion 11 including the coil unit 3 and the plurality of wires 25 is covered with a tube 31. The tube 31 is a sheath member made of, for example, PTFE (polytetrafluoroethylene) provided so as to cover the plurality of accommodation members 2 from the distal end accommodation member 2a to the accommodation member 2 on the proximal end side. The plurality of wires 25 from other coil units 3 accommodated in other accommodation portions 11 provided closer to the distal end side of the probe 1 than the accommodation portion 11 shown in FIG. 11 pass through the inside of the tube 31 on the outer circumferential side of the coil unit 3.

Note that a plurality of items included in the tube 31 of the accommodation portion 11 are the coil unit 3, the accommodation member 2 and the plurality of wires 25. When a plurality of accommodation members 2 connected together and mounted with the respective coil units 3 are passed through the tube 31, it has been proven through an experiment of the present applicant that a filling factor of the included items in the tube 31 in the concave portion 11c is preferably 55% to 80% to facilitate the insertion of the plurality of accommodation members 2.

More specifically, when, for example, 12 coil units 3 are mounted on the distal end side portion R1 of the probe 1, a filling factor α expressed in following equation (1) is preferably within a range of 0.55 to 0.8 when it is assumed that the cross-sectional area of the inner diameter portion of the tube 31 is S1, the cross-sectional area of the coil unit 3 is s1, the cross-sectional area of the base portion 11a is s2 and the sum of all cross-sectional areas of the plurality of wires 25 is s3.

$$\alpha=(s1+s2+s3)/S1 \qquad \text{Expression (1)}$$

Particularly, when the filling factor α exceeds 0.8 (that is, 80%), it is difficult to pass the accommodation member 2 through the inside of the tube 31 which is a sheath member and operability deteriorates, and therefore the filling factor α is preferably 0.8 or less.

Next, the configurations of the connection portions 13 and 14 will be described.

Figure 12:
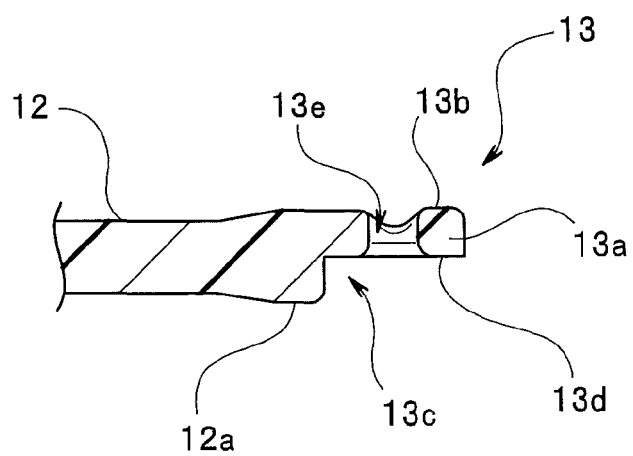
FIG. 12 is a cross-sectional view of a connection portion 13 along an axial direction of an axial portion 12 according to the first embodiment of the present invention.

First, the configurations of the connection portions 13 provided at the proximal end portion of the distal end accommodation member 2a and at the proximal end portion of the accommodation member 2 will be described. FIG. 12 is a cross-sectional view of the connection portion 13 along the axial direction of the axial portion 12. As shown in FIG. 12, the connection portion 13 has an extending portion 13a that extends in the proximal end direction from an expansion portion 12a on the proximal end side of the axial portion 12 at the proximal end portion of the distal end accommodation member 2a and at the proximal end portion of the accommodation member 2.

The distance of the surface portion 13b on the upper side of the extending portion 13a from the axial center of the axial portion 12 is the same as the distance of the surface portion of the expansion portion 12a which is continuous to the axial portion 12 from the axial center of the axial portion 12. The underside of the extending portion 13a has a stepped portion 13c and a flat portion 13d parallel to the axial direction of the axial portion 12 of the stepped portion 13c.

As shown in FIG. 12, a hole portion 13e is provided in the center of the extending portion 13a formed in the vertical direction orthogonal to the axial direction of the axial portion 12.

Figure 13:
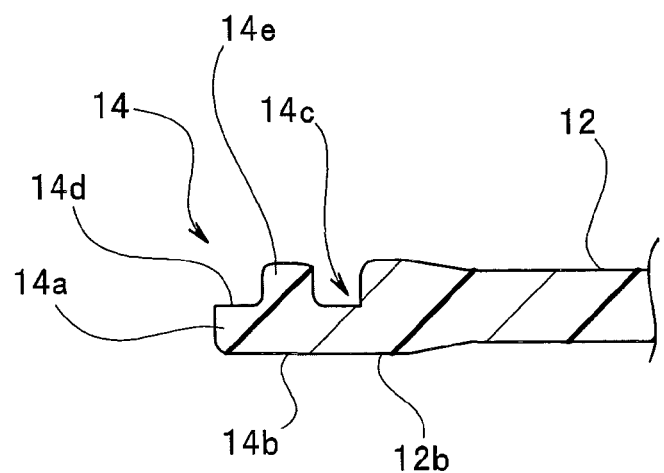
FIG. 13 is a cross-sectional view of a connection portion 14 along the axial direction of the axial portion 12 according to the first embodiment of the present invention.

FIG. 13 is a cross-sectional view of a connection portion 14 along the axial direction of the axial portion 12. As shown in FIG. 13, the connection portion 14 has an extending portion 14a that extends in the distal end direction from an expansion portion 12b of the axial portion 12 on the distal end side at the distal end portion of the accommodation member 2.

The distance of a surface portion 14b on the underside of the extending portion 14a from the axial center of the axial portion 12 is the same as the distance of the surface portion of the expansion portion 12b which is continuous to the axial portion 12 from the axial center of the axial portion 12. The upper side of the extending portion 14a includes a stepped portion 14c and a flat portion 14d parallel to the axial direction of the axial portion 12 of the stepped portion 14c.

As shown in FIG. 13, a protruding portion 14e is provided in the center of the extending portion 14a formed in a direction orthogonal to the axial direction of the axial portion 12 so as to protrude upward. The protruding portion 14e has a columnar shape, the aforementioned hole portion 13e of the extending portion 13a has a circular cross section, the protruding portion 14e has the same circular cross section as that of the hole portion 13e and is formed to be insertable into the hole portion 13e.

By applying an adhesive to the flat portion 13d of the extending portion 13a or the flat portion 14d of the extending portion 14a, fitting the protruding portion 14e into the hole portion 13e, connecting the connection portions 13 and 14 and bonding the flat portion 13d and the flat portion 14d together in close contact, it is possible to connect the distal end accommodation member 2a and the accommodation member 2, and between the accommodation members 2. That is, the connection portions 13 and 14 are connected together by engaging the protruding portion 14e provided at one end of one accommodation member 2 with the hole portion 13e provided at one end of another accommodation member 2 connected to the one accommodation member.

In manufacturing of the probe 1, when the distal end accommodation member 2a is placed on a work bench in such a way that the bottom surfaces 11a1 of the four accommodation portions 11 of the distal end accommodation member 2a face upward, the worker can accommodate the coil unit 3 in the concave portion 11c of each accommodation portion 11 by causing the coil unit 3 to engage with the concave portion 11c.

At this time, since the bottom surface 11a1 of the base portion 11a has a curved surface shape that matches the surface shape of the coil unit 3, the coil unit 3 is mounted on the accommodation portion 11 in close contact therewith.

Furthermore, regarding the accommodation member 2 connected to the distal end accommodation member 2a, when the distal end accommodation member 2a is placed on the work bench in such a way that the bottom surface 11a1 of the accommodation portion 11 faces upward, the worker can accommodate the coil unit 3 in each accommodation portion 11 by causing the coil unit 3 to engage with the accommodation portion 11.

Furthermore, as shown in FIG. 2 to FIG. 5, when the plurality of accommodation members 2 (including the distal end accommodation member 2a) are connected together via the connection portions 13 and 14, their normal directions with respect to the bottom surface 11a1 of each base portion 11a that contacts the coil unit 3 are the same. Therefore, the coil unit 3 can be placed on the accommodation portion 11 more easily.

Furthermore, the bottom surface 11a1 of the accommodation portion 11 and the protruding portion 14e of the connection portion 14 face the same direction, that is, the upward direction. Thus, when the distal end accommodation member 2a and the accommodation member 2 are placed on the work bench so that the bottom surface 11a1 of each accommodation portion 11 faces upward, the protruding portion 14e of the connection portion 14 faces upward and the axis of the hole portion 13e of the connection portion 13 also faces the vertical direction, thus facilitating the operation of bonding and connecting the connection portions 13 and 14.

Moreover, the distal end accommodation member 2a is different in length from the accommodation member 2 and the plurality of accommodation members 2 have the same configuration, which allows the worker to easily distinguish the distal end accommodation member 2a from the accommodation member 2 and also provides excellent operability.

Note that here, the connection portion 13 may be a concave portion with which the protruding portion 14e engages instead of the hole portion 13e.

Moreover, the distal end accommodation member 2a may have the connection portion 14 instead of the connection portion 13 at the proximal end portion and the accommodation member 2 may have the connection portion 13 on the distal end side and the connection portion 14 on the proximal end side.

Figure 14:
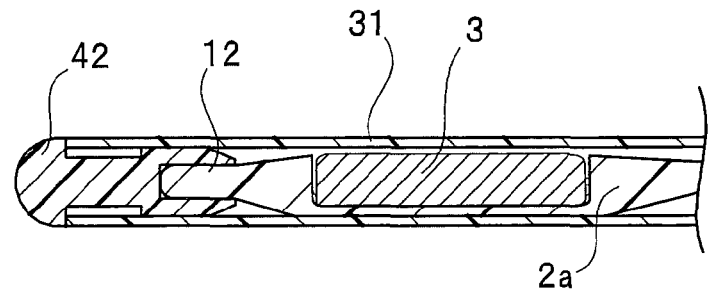
FIG. 14 is a cross-sectional view illustrating a configuration of a distal end of the probe 1 according to the first embodiment of the present invention.

FIG. 14 is a cross-sectional view illustrating a configuration of the distal end of the probe 1.

The axial portion 12 of the distal end accommodation member 2a on the distal end side is covered with a distal end cap member 42. The axial portion 12 and the distal end cap member 42 are bonded together using an adhesive (not shown). The proximal end portion of the distal end cap member 42 is covered with the tube 31.

Figure 15:
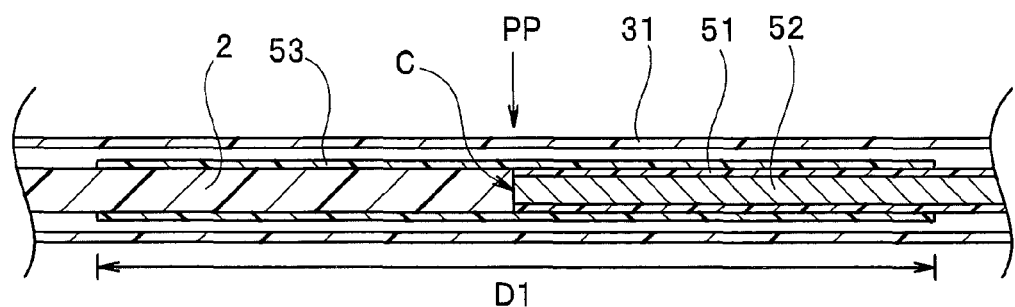
FIG. 15 is a cross-sectional view illustrating a connection between the accommodation member 2 closest to the proximal end side in the probe 1 and a wire member on the proximal end side according to the first embodiment of the present invention.

FIG. 15 is a cross-sectional view illustrating a connection between the accommodation member 2 closest to the proximal end side in the probe 1 and a wire member on the proximal end side.

As shown in FIG. 15, the axial portion 12 at the proximal end portion of the accommodation member 2 closest to the proximal end side within the probe 1 and the distal end portion of the wire member 52 covered with a thermal contraction tube 51 are bonded and fixed using an adhesive member. For example, the connection portion 13 at the proximal end portion of the accommodation member 2 is cut, and the end face of the cut axial portion 12 and the end face of the distal end portion of a wire member 52 are bonded together using an adhesive.

Furthermore, the proximal end portion of the accommodation member 2 and the distal end portion of the wire member 52 connected together are covered with a thermal contraction tube 53 by a predetermined length D1 along the axial direction of the probe 1. As shown in FIG. 15, the thermal contraction tube 53 having the length D1 covers the proximal end portion of the accommodation member 2 and the distal end portion of the wire member 52 so as to include a bonding portion C between the two portions. Furthermore, the thermal contraction tube 53, the thermal contraction tube 51 and the accommodation member 2 are fixed using an adhesive. The wire member 52 is bendable but is a metallic wire member made of a metal stranded wire such as stainless steel and is more rigid than the accommodation member 2. Note that the wire member 52 may also be made of resin.

In FIG. 1 and FIG. 15, the distal end side portion R1 closer to the distal end side than a position PP of the bonding portion C of the probe 1 is made up of the distal end accommodation member 2a made of silicon rubber or the like and the plurality of accommodation members 2, and is therefore flexible, whereas the proximal end side portion R2 closer to the proximal end side than the position PP of the bonding portion C of the probe 1 is more rigid than the distal end side portion R1 because it has the metallic wire member 52 passed therethrough.

Thus, the distal end side portion R1 of the probe 1 is flexible and easily bendable, whereas the proximal end side portion R2 is also bendable but more rigid than the distal end side portion R1. As a result, when the probe 1 is inserted into the treatment instrument insertion channel of the endoscope, when the distal end portion of the probe 1 reaches the bending portion of the endoscope insertion portion, the probe 1 is less likely to be buckled on the operator side.

Figure 16:
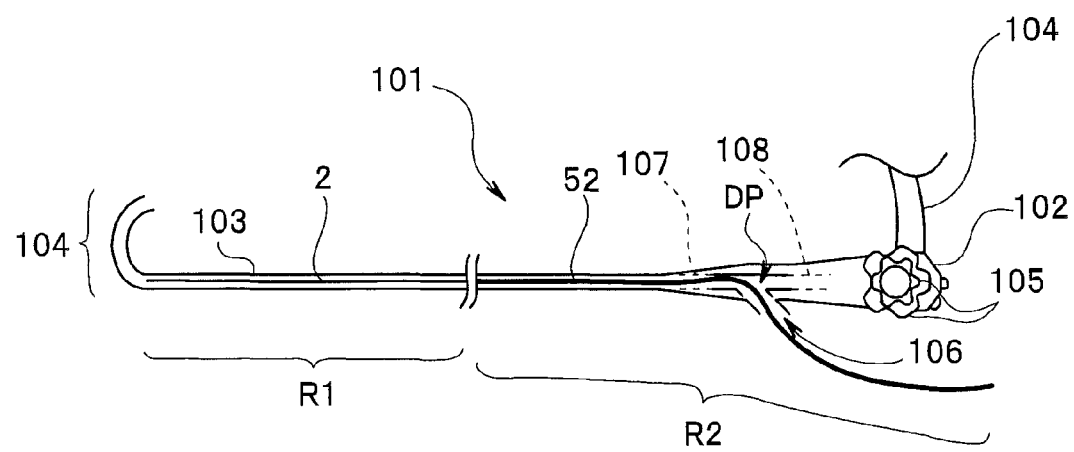
FIG. 16 is a schematic view illustrating a state when the probe 1 according to the first embodiment of the present invention is inserted into a treatment instrument insertion channel 107 of an endoscope 101 and the distal end portion of the probe 1 reaches a proximal end portion of a bending portion 104 of an endoscope insertion portion 103.
Figure 17:
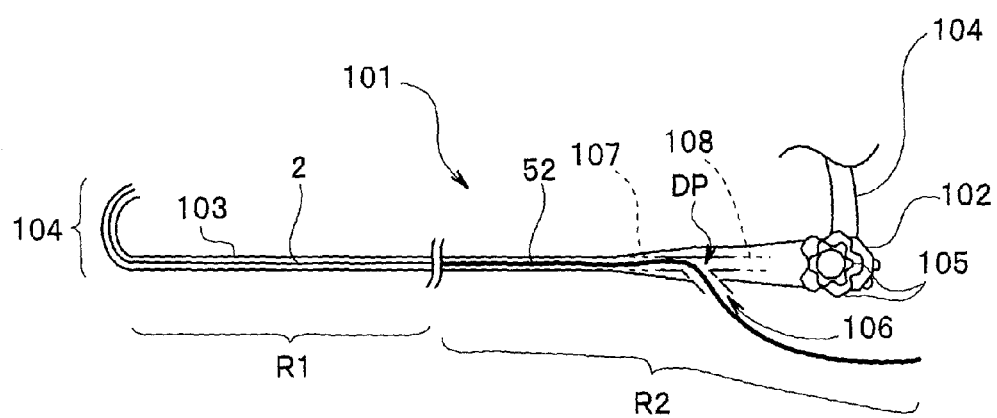
FIG. 17 is a schematic view illustrating a state when the probe 1 according to the first embodiment of the present invention is inserted into the treatment instrument insertion channel 107 of the endoscope 101 and the distal end portion of the probe 1 reaches the distal end portion of the bending portion 104 of the endoscope insertion portion 103.

FIG. 16 and FIG. 17 are diagrams illustrating the operation of the probe 1 inserted into the endoscope. FIG. 16 is a schematic view illustrating a state when the probe 1 is inserted into a treatment instrument insertion channel 107 of an endoscope 101 and a distal end portion of the probe 1 reaches a proximal end portion of a bending portion 104 of an endoscope insertion portion 103. FIG. 17 is a schematic view illustrating a state when the probe 1 is inserted into the treatment instrument insertion channel 107 of the endoscope 101 and the distal end portion of the probe 1 reaches the proximal end portion of the bending portion 104 of the endoscope insertion portion 103.

The endoscope 101 is configured by including an operation section 102, the insertion portion 103 that extends from the operation section 102 and a universal connector 102a that extends from the operation section 102. The distal end portion of the insertion portion 103 includes the bending portion 104. By operating a bending knob 105 provided on the operation section 102, it is possible to bend the bending portion 104 and change the orientation of the distal end portion of the insertion portion 103 in vertical and horizontal directions.

The probe 1 can be inserted from a forceps port 106 provided on the distal end side of the operation section 102 of the endoscope 101 and inserted into the treatment instrument insertion channel 107. The treatment instrument insertion channel 107 is branched on the proximal end side and one portion communicates with the forceps port 106 and the other communicates with a suction channel 108. Thus, as shown in FIG. 16, the treatment instrument insertion channel 107 is branched at a branch portion DP into the forceps port 106 and the suction channel 108.

When the probe 1 is inserted from the forceps port 106 toward the treatment instrument insertion channel 107 diagonally with respect to the axis of the insertion portion 103, the probe 1 is inserted into the treatment instrument insertion channel 107 with the distal end portion of the probe 1 contacting the inner wall at the branch portion DP of the treatment instrument insertion channel 107. The operator further pushes the probe 1 into the forceps port 106, and can thereby cause the distal end portion of the probe 1 to reach the bending portion 104 of the insertion portion 103.

As shown in FIG. 16, when the distal end portion of the probe 1 reaches the proximal end portion of the curved bending portion 104, a proximal end portion R2 of the probe 1 including the metallic wire member 52 passes through the branch portion DP and protrudes from the forceps port 106.

As shown in FIG. 16, when the distal end portion of the probe 1 reaches the proximal end portion of the curved bending portion 104, the distal end portion of the probe 1 comes into contact with the inner wall of the bending portion 104, and therefore the resistance increases when the operator further pushes the probe 1 into the forceps port 106.

However, since the proximal end portion R2 closer to the proximal end than the aforementioned position PP of the probe 1 incorporates the metallic wire member 52, when the operator pushes the probe 1 into the forceps port 106, the probe 1 is unlikely to be budded.

Thus, the probe 1 is further pushed into the treatment instrument insertion channel 107 with the distal end portion of the probe 1 contacting the inner wall of the curved bending portion 104, but since the portion R1 closer to the distal end side than the aforementioned position PP of the probe 1 is configured by connecting the flexible accommodation members 2, the distal end portion of the probe 1 can easily move forward through the bending portion 104.

Furthermore, as shown in FIG. 17, when the distal end portion of the probe 1 reaches the distal end portion of the bending portion 104 of the endoscope insertion portion 103, since the flexible distal end side portion R1 has been inserted into the bending portion 104, the operator does not need much power to operate the bending knob 105 of the operation section 102.

As described above, according to the probe of the aforementioned embodiment, it is possible to prevent breakage of the wire that extends from the coil which is an electronic part.

Furthermore, the probe 1 is configured by connecting the plurality of accommodation members and the normal direction is the same with respect to the plane on which the protruding portion of the connection portion is formed (or plane on which a hole portion is formed). That is, the normal direction of the plane of the flat portion 14d on which the protruding portion 14e of each accommodation member 2 is formed or the plane of the flat portion 13d on which the hole portion 13e is formed is the same for the plurality of connected accommodation members 2 and the distal end accommodation member 2a. Therefore, the worker can thereby perform connection operation easily.

Furthermore, in the connected plurality of accommodation members 2 and distal end accommodation member 2a, when the coil unit 3 which is an electronic part is accommodated in the accommodation portion 11, since the normal direction is the same with respect to the bottom surfaces 11a1 of the base portions 11a of all the accommodation portions 11, that is, the bottom surfaces 11a1 of the base portions 11a of all the accommodation portions 11 face the same direction, it is only necessary to accommodate the electronic parts so as to engage with the concave portions of the accommodation portions 11, which facilitates the operation of mounting the electronic parts on the probe 1 and also reduces the number of machining man-hours.

In other words, the probe of the present embodiment is easy to assemble.

Second Embodiment

The probe according to the first embodiment has a configuration in which a plurality of electronic part accommodation members each made up of the integrally molded accommodation portion and axial portion are connected together. A probe according to a second embodiment has a configuration in which a plurality of accommodation members making up an accommodation portion and a plurality of axial members making up an axial portion are connected together.

Hereinafter, the probe of the present embodiment will be described. Description of the same components as those of the first embodiment will be omitted and different components will be described.

Figure 18:
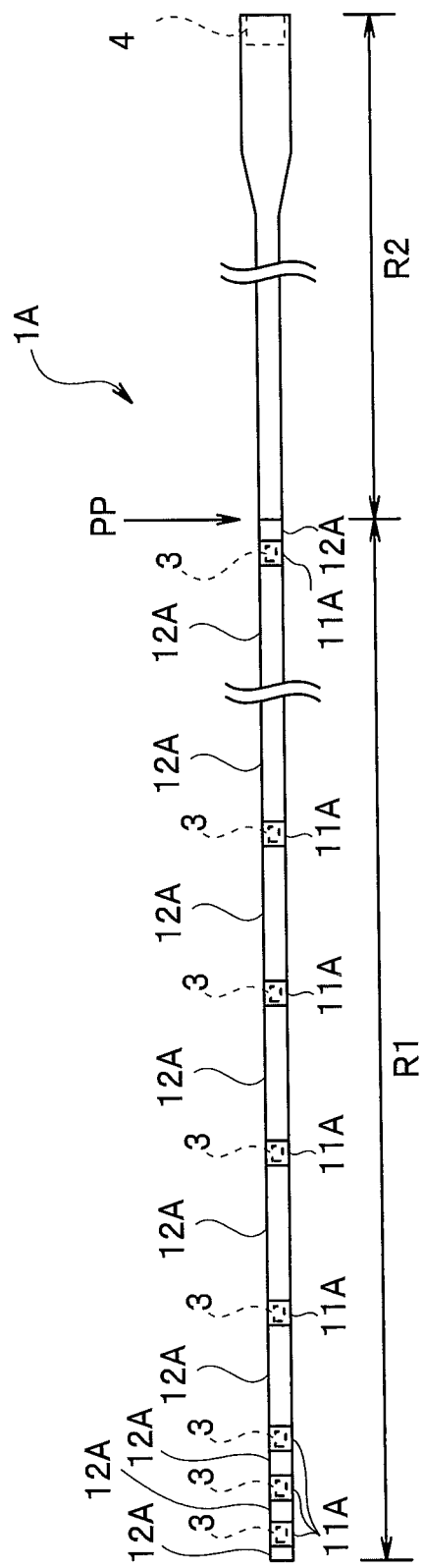
FIG. 18 is a schematic configuration diagram illustrating an overall configuration of a probe according to a second embodiment of the present invention.

FIG. 18 is a schematic configuration diagram illustrating an overall configuration of the probe according to the present embodiment.

A probe 1A is an endoscope insertion shape observation probe. A distal end side portion R1 of the probe 1A is an elongated flexible portion made up of a plurality of axial members 12A and a plurality of accommodation members 11A alternately arranged and connected together with their outer circumferential portions covered with a sheath member. The accommodation member 11A making up the accommodation portion and the axial member 12A making up the axial portion are separate members. Note that the sheath member is not shown in FIG. 18. A proximal end side portion R2 of the probe 1A has a configuration similar to that of the first embodiment.

Figure 19:
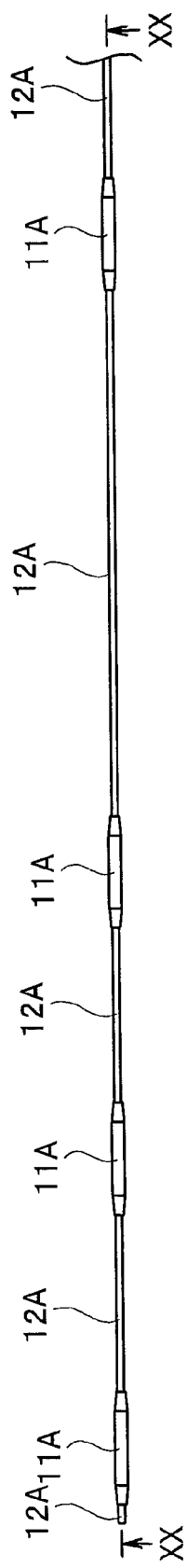
FIG. 19 is a plan view of a distal end portion of a distal end side portion R1 of a probe 1A according to the second embodiment of the present invention.
Figure 20:
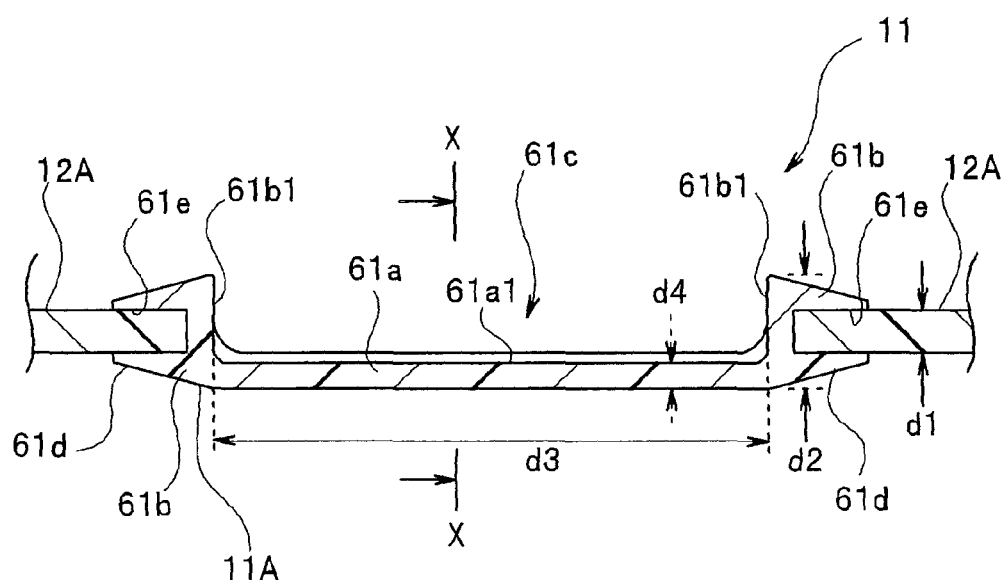
FIG. 20 is a cross-sectional view of an accommodation member 11A along a line XX-XX in FIG. 19.

FIG. 19 is a plan view of a distal end portion of the distal end side portion R1 of the probe 1A. FIG. 20 is a cross-sectional view of the accommodation member 11A along a line XX-XX in FIG. 19. Note that FIG. 19 and FIG. 20 do not show the sheath member such as a tube.

As shown in FIG. 19 and FIG. 20, the distal end side portion R1 of the probe 1A is constructed of the plurality of axial members 12A and the plurality of accommodation members 11A alternately connected together.

The accommodation member 11A is made of resin such as polycarbonate and is a rigid material formed through integral molding. Note that the accommodation member 11A may be metallic such as stainless steel.

As shown in FIG. 20, the accommodation member 11A includes a base portion 61a and two wall portions 61b provided to stand upright upward from the base portion 61a at both ends in the longitudinal direction of the base portion 61a.

More specifically, in order to accommodate the coil unit 3 which is an electronic part having a predetermined length and a predetermined height, the accommodation member 11A includes an accommodation portion 11 provided with the base portion 61a having a length substantially equal to the predetermined length in the longitudinal direction of the probe 1A and the two wall portions 61b provided to stand upright at a height substantially equal to the predetermined height of the coil unit 3 from the base portion 61a at both ends of the base portion 61a in the longitudinal direction of the probe 1A. Furthermore, the accommodation member 11A includes the accommodation portion 11 in which the base portion 61a and the wall portions 61b are integrally formed.

In the accommodation portion 11, a bottom surface 61a1 of the base portion 61a and two opposite wall surfaces 61b1 of the two wall portions 61b form a concave portion 61c to accommodate the coil unit 3. A tapered portion 61d which is an expansion portion is provided between the wall portion 61b and the axial member 12A. As shown in FIG. 20, the tapered portions 61d are provided on both wall portions 61b and the cross-sectional shape on the wall surface 61b1 side is greater than the cross-sectional shape on the axial member 12A side. The tapered portion 61d has a shape whose outer dimension gradually decreases from the wall surface 61b1 toward the axial portion 12.

The bottom surface 61a1 of the base portion 61a has a trough-shaped curved surface along the axial direction in such a way that the shape of the cross section orthogonal to the longitudinal axis of the accommodation member 11A becomes part of a circle.

The shape of the concave portion 61c is the same as the shape of the concave portion 11c of the accommodation portion 11 of the first embodiment shown in FIG. 10 and the sizes of the respective components of the accommodation member 11A are the same as the respective sizes d1, d2, d3 and d4 shown in FIG. 10.

Moreover, a bore portion 61e into which the axial member 12A is fitted is provided at an end of each tapered portion 61d.

Each axial member 12A is made of metal or resin and has the same shape as that of the cross section orthogonal to the axis of the axial member 12A of the bore portion 61e. The axial member 12A is fitted into the bore portion 61e and fixed using an adhesive. In this way, the axial member 12A extends from the bore portion 61e of the wall portion 61b in the longitudinal direction of the probe 1A and connects between a plurality of accommodation members 11A.

Each axial member 12A has such a length in the axial direction that the plurality of coil units 3 are arranged at the same interval as that of the first embodiment. Thus, the distance between the coil units 3 from the distal end to the third coil unit is shorter than the distance between the coil units 3 from the fourth and subsequent coil units 3 from the distal end.

Furthermore, the proximal end side portion R2 of the probe 1A of the present embodiment is bendable but is more rigid than the distal end side portion R1 because a wire member is passed therethrough. The connection portion between the distal end side portion R1 and the proximal end side portion R2 of the probe 1A has a configuration similar to that of the first embodiment shown in FIG. 15.

As described above, according to the aforementioned probe of the present embodiment, it is possible to prevent breakage of the wire extending from the coil which is an electronic part.

Note that although the aforementioned two embodiments have described examples of the probe inserted through the treatment instrument insertion channel of the endoscope, the probe of the aforementioned two embodiments may be incorporated in the insertion portion of the endoscope.

The present invention is not limited to the aforementioned embodiments but various changes, modifications or the like can be made without departing from the spirit and scope of the present invention.

The aforementioned two embodiments have described examples of an endoscope insertion observation probe which is a medical probe, but the probe of the present invention is applicable to medical probes other than endoscope insertion observation probes. For example, it is applicable to an ultrasound probe that performs multipoint simultaneous diagnosis using, for example, a plurality of ultrasound transducers as electronic parts.

What is claimed is:

1. A probe insertable through a channel provided in an endoscope insertion portion or incorporated in the endoscope insertion portion, the probe comprising:
   a plurality of elongated accommodation members, each comprising:
      one or more accommodation portions, each of the one or more accommodation portions accommodating an electronic part, where each of the electronic parts having a predetermined length and a predetermined height, each of the one or more accommodation portions having a base portion having a length in a longitudinal direction substantially equal to the predetermined length of the electronic part and a wall portion provided at each of both ends of the base portion in the longitudinal direction having a height from the base portion substantially equal to the predetermined height of the electronic part, the base portion and the two wall portions being integrally formed so as to define a concave portion for engagingly accommodating the electronic part from a direction orthogonal to an axis of the accommodation member; and
      an axial portion that extends in the longitudinal direction from at least one of the wall portions to connect to at least one other of the plurality of accommodation members,
   wherein, in a state where the plurality of the accommodation members are connected together, a normal direction with respect to a bottom surface of each base portion that contacts each electronic part is the same, and
   wherein in a state where the electronic part is accommodated in the accommodation portion, a width of the base portion in a direction orthogonal to the axis of the accommodation member as the each electronic part is viewed from the normal direction is equal to or less than a width of the each electronic part in the direction orthogonal to the axis of the accommodation member.

2. The probe according to claim 1, wherein the wall portions have a tapered portion in the longitudinal direction of the probe.

3. The probe according to claim 1, wherein the probe is configured by connecting the plurality of accommodation members formed by being united with one or two or more axial portions.

4. The probe according to claim 3, wherein a connection in a connection portion is performed by causing a protruding portion provided at one end of one accommodation member to engage with a hole portion or a concave portion provided at one end of the other accommodation member connected to the one accommodation member.

5. The probe according to claim 4, wherein a normal direction with respect to a plane on which the protruding portion in the each accommodation member is formed or a plane on which the hole portion or the concave portion is formed is the same for the plurality of accommodation members.

6. The probe according to claim 1, wherein the plurality of accommodation members and the plurality of axial portions are each separate members.

7. The probe according to claim 1, wherein a contact surface of the base portion that comes into contact with the electronic part when the electronic part is placed comprises a curved surface along an outer circumferential surface of the electronic part that contacts the base portion.

8. The probe according to claim 7, wherein the wall portions partially have an edge shape along a cross-sectional shape of the electronic part orthogonal to the longitudinal direction when the electronic part is placed.

9. The probe according to claim 8, wherein when the cross-sectional shape of the electronic part orthogonal to the longitudinal direction when the electronic part is placed is circular, the cross-sectional shape of the curved surface orthogonal to the longitudinal direction matches an arc which is a part of the circle and the edge shape also matches an arc of another part of the circle.

10. The probe according to claim 1, wherein the probe is an endoscope insertion shape observation probe.

11. The probe according to claim 1, wherein the electronic part is a magnetic coil.

12. The probe according to claim 1, wherein the probe is a multipoint simultaneous diagnosis ultrasound probe using a plurality of ultrasound transducers as the electronic parts.

13. An endoscope comprising the probe according to claim 1 incorporated in the endoscope insertion portion.

14. The probe according to claim 1, wherein a distal most accommodation member comprises a plurality of accommodation portions.

15. The probe according to claim 1, further comprising a connector connected to a proximal most accommodation member.

16. The probe according to claim 1,
- wherein a connection in a connection portion at adjacent two accommodation members is performed by causing a protruding portion provided at one end of one accommodation member to engage with a hole portion or a concave portion provided at one end of the other accommodation member connected to the one accommodation member, and
- wherein in a state where a plurality of the accommodation members are connected together, a normal direction with respect to a plane on which the protruding portion in the each accommodation member is formed or a plane on which the hole portion or the concave portion is formed is the same as a normal direction for a bottom surface of the each base portion.

\* \* \* \* \*